United States Patent
Mentkow et al.

(10) Patent No.: US 11,147,785 B2
(45) Date of Patent: Oct. 19, 2021

(54) MODIFIED FREE AMINO ACID FORMULATION AND USES

(71) Applicants: Jack Mentkow, Wellington, FL (US); Lisa Mentkow, Wellington, FL (US)

(72) Inventors: Jack Mentkow, Wellington, FL (US); Lisa Mentkow, Wellington, FL (US)

(*) Notice: Subject to any disclaimer, the term of this patent is extended or adjusted under 35 U.S.C. 154(b) by 0 days.

(21) Appl. No.: 17/209,786

(22) Filed: Mar. 23, 2021

(65) Prior Publication Data

US 2021/0290572 A1    Sep. 23, 2021

Related U.S. Application Data

(60) Provisional application No. 63/100,658, filed on Mar. 23, 2020, provisional application No. 63/101,052, filed on Apr. 15, 2020.

(51) Int. Cl.

| | | |
|---|---|---|
| *A61K 31/195* | (2006.01) | |
| *A61K 31/198* | (2006.01) | |
| *A61K 47/02* | (2006.01) | |
| *A61K 47/32* | (2006.01) | |
| *A61K 9/00* | (2006.01) | |
| *A61K 47/10* | (2017.01) | |

(52) U.S. Cl.
CPC .......... *A61K 31/198* (2013.01); *A61K 9/0014* (2013.01); *A61K 9/0053* (2013.01); *A61K 47/02* (2013.01); *A61K 47/10* (2013.01); *A61K 47/32* (2013.01)

(58) Field of Classification Search
CPC .................................................... A61K 31/195
USPC ...................................................... 514/561
See application file for complete search history.

(56) References Cited

PUBLICATIONS

A. M. Benjamin, et al., "Fate of L-Glutamate in the Brain", Journal of Neurochemistry—Wiley Online Library / vol. 23, Issue 3 / p. 457-464, First published: Sep. 1974, https://doi.org/10.1111/j.1471-4159.1974.tb06046.x.

Z.-H. Wen, et al., "Osteoarthritis and Cartilage", Excitatory amino acid glutamate: role in peripheral nociceptive transduction and inflammation in experimental and clinical osteoarthritis, 23 (2015), p. 2009-2016, Accepted: Mar. 18, 2015.

Gisele P. Oliveira, et al., "Exogenous Glutamine in Respiratory Diseases: Myth or Reality?", Published online Feb. 4, 2016 p. 1/19, https://www.ncbi.nlm.nih.gov/pmc/articles/PMC4772040/.

Robert W. Cowan, et al., "Frontiers | Glutamate Signaling in Healthy and Diseased Bone | Endocrinology", https://www.frontiersin.org/articles/10.3389/fendo.2012.00089/full, Published: Jul. 19, 2012, p. 1/16.

Anna-Kari Hajati, et al., "Endogenous glutamate in association with inflammatory and hormonal factors modulates bone tissue resorption of the temporomandibular joint in patients with early rheumatoid arthritis", https://www.ncbi.nlm.nih.gov/pmc/articles/PMC2771262/, p. 1/18, Published in final edited form as: J Oral Maxillofac Surg. Sep. 2009; 67(9): 1895-1903.

Satyajit Dutta, et al., "Glutamic acid as anticancer agent: An overview", https://www.ncbi.nlm.nih.gov/pmc/articles/PMC3824943/, p. 1/11, Saudi Pharm J. Oct. 2013; 21(4): 337-343., doi: 10.1016/j.jsps.2012.12.007.

Fernstrom J.D., "Annals of Nutrition and Metabolism", https://doi.org/10.1159/000494782, Ann Nutr Metab 2018;73 (suppl 5):43-52.

S. P. Bessmann, et al., "The Absorption of Glutamic Acid and Glutamine", This is an Open Access article under the CB BY license, Published: Apr. 15, 948, p. 817-823.

"Re-evaluation of glutamic acid (E 620), sodium glutamate (E 621), potassium glutamate (E 622), calcium glutamate (E 623), ammonium glutamate (E 624) and magnesium glutamate (E 625) as food additives", www.efsa.europa.eu/efsajournal, EFSA Journal 2017;15(7):4910, Adopted: Jun. 21, 2017, p. 1/90.

*Primary Examiner* — Raymond J Henley, III
(74) *Attorney, Agent, or Firm* — Laurence A. Greenberg; Werner H. Sterner; Ralph E. Locher

(57) ABSTRACT

A composition and methods of administration are provides utilizing Monosodium L-Glutamate Monohydrate in a stabilized form at an alkaline pH.

11 Claims, No Drawings

MODIFIED FREE AMINO ACID FORMULATION AND USES

INDEX TO RELATED APPLICATIONS

This application is a non-provisional application and claims benefit to each of U.S. Provisional Patent Application Ser. No. 63/100,658 filed Mar. 23, 2020 and U.S. Provisional Patent Application Ser. No. 63/101,052 filed Apr. 15, 2020 the disclosures being incorporated herewith by reference in their entirety.

BACKGROUND OF THE INVENTION

The events of the year 2020 greatly accentuated the advancements and continuing need in the medicinal and healing arts.

Yet, as science progresses with such innovations as mRNA vaccines, there are often relatively simple and straightforward therapies that are also discovered.

There is a always a need for novel medicinal therapies and even more so for these therapies to be simple, yet effective.

The present invention fits such a need.

SUMMARY OF THE INVENTION

The present invention has surprisingly discovered a simple and straightforward medical application for Monosodium L-Glutamate Monohydrate (CAS Number: 6106-04-3, hereinafter, MSLGM). While generally known as a food additive, there has been little researched relating to any medicinal uses. In fact, even though studies have proven to the contrary, there is still a widely held belief that use causes headaches (a phenomena also known as "Chinese Restaurant Syndrome" due to the widespread us in Chinese foods). So while the world runs away from monosodium glutamate, the inventors of the subject invention have run towards it.

One aspect that is advantageous in the present invention is a preferred embodiment of a "free" amino acid (which does not require FDA approval because it is already listed as GRAS).

The present invention further contemplates MSLGM be "alone or in combination . . . " meaning MSLGM alone or in combination with other free amino acids, creating longer amino acid chains such as peptides, fragmented proteins, proteins etc. for medicinal use.

In one embodiment, the present invention is an oral liquid composition comprising:
Monosodium L-Glutamate Monohydrate 5-10% w/w;
Water 90-95% w/w;
NaOH q.s. to adjust pH to between 7.5-9.0.

In one embodiment, the present invention Monosodium L-Glutamate Monohydrate contains not less than 99% relative to H2O on a dried basis based on a non-aqueous titration.

In one embodiment, the present invention the Monosodium L-Glutamate Monohydrate is 7.5-8.6% w/w.

In one embodiment, the present invention the Monosodium L-Glutamate Monohydrate is 8.2-8.5% w/w.

In one embodiment, the present invention the water is 92-93% w/w.

In one embodiment, the present invention is an oral liquid composition consisting of:
Monosodium L-Glutamate Monohydrate 5-10% w/w;
Water 90-95% w/w;
NaOH q.s. to adjust pH to between 7.5-9.0.

In one embodiment, the present invention is an oral liquid composition consisting of:
Monosodium L-Glutamate Monohydrate 7-8% w/w;
Water 92-93% w/w;
NaOH q.s. to adjust pH to between 7.5-9.0.

In one embodiment, the present invention is a topical composition comprising:
Monosodium L-Glutamate Monohydrate 540-840 g;
H2O 2200-3800 g;
Propylene Glycol 300-500 g;
polyacrylamide based emulsion and rheology modifier—400-600 g;
NaOH q.s. to 7.5-9.0 pH.

In one embodiment, the present invention is a topical composition comprising:
Monosodium L-Glutamate Monohydrate 680-720 g;
H2O 2700-3000 g;
Propylene Glycol 380-420 g;
polyacrylamide based emulsion and rheology modifier 480-520 g;
NaOH q.s. to 8.5 pH.

In one embodiment, the present invention is a topical composition comprising:
Monosodium L-Glutamate Monohydrate 700 g;
H2O—2800 g;
Propylene Glycol 400 g;
polyacrylamide based emulsion and rheology modifier 510 g;
NaOH q.s. to 8.5 pH.

In one embodiment, the present invention is a topical composition consisting of:
Monosodium L-Glutamate Monohydrate 540-840 g;
H2O 2200-3800 g;
Propylene Glycol 300-500 g;
polyacrylamide based emulsion and rheology modifier—400-600 g;
NaOH q.s. to 7.5-9.0 pH.

In one embodiment, the present invention is a topical composition consisting of:
Monosodium L-Glutamate Monohydrate 680-720 g;
H2O 2700-3000 g;
Propylene Glycol 380-420 g;
polyacrylamide based emulsion and rheology modifier 480-520 g;
NaOH q.s. to 8.5 pH.

In one embodiment, the present invention is a topical composition consisting of:
Monosodium L-Glutamate Monohydrate 700 g;
H2O—2800 g;
Propylene Glycol 400 g;
polyacrylamide based emulsion and rheology modifier 510 g;
NaOH q.s. to 8.5 pH.

The invention further includes a method of treating, preventing or ameliorating a human patient, said method comprising the steps of:
identifying a patient with at least one of Gout, Arthritis, Shingles, Acne, Herpes I, Herpes II, Sarcoidosis, Cirrhosis, Prostate-PSA, Prostate Cancer, Mitral/Aortic Valve Calcification, Peyronie's Disease, Cataracts, Sebaceous Growths-COVID-19—Prevention, Cure, triggers self immunity, or Kidney Stones;
administering as appropriate orally, topically, nasally or via injection, a composition according to any embodiment of the invention described herein, wherein said administering must be in a fasting state either two hours after food consumption or two hours prior to food consumption;
optionally, administering subsequent doses as indicated by clinical observation.

DETAILED DESCRIPTION OF THE PREFERRED EMBODIMENT

In a one preferred embodiment of the formulation and method of use.

The invention uses Monosodium L-Glutamate Monohydrate (EFC-Extra Fine Crystals) described herein contains not less than 99% relative to H2O on a dried basis (non-aqueous titration).

The dry powder is dissolved in purified water using a ratio of 10 grams to 118 ml. This purified "free" amino acid is then modified and beneficiated by the addition of an alkali to a pH of 8.5. This allows the solution to remain stable, prevents recrystallization, increases bioavailability, metabolization and absorption, all without the use of heat which would compromise the active ingredient efficacy.

This is a novel formulation as current science and available information provide that only heat could solubilize MSLGM in water and that it would quickly recrystallize when used in concentrations as desired in the present formulations.

As FDA and USP require significant stability and shelf life of preparations, it appeared as if MSLGM would not be suitable for use as such.

Yes, surprisingly, the present invention has discovered that adjustment of the solution to pH 7.0-9.0 prevented recrystallization that would otherwise be expected in a solution of this concentration.

Once the problem of stability is successfully addressed, the present invention addresses the problem relating to bioavailability. It is well-known in the pharmaceutical arts that certain molecules have decreased bioavailability when administered with food. MSLGM requires oral dosages being administered without food (2 hours before and after ingestion). This prevents the free amino acid from binding with the proteins in the food, rendering it ineffective as medically beneficial. Although MSG has a long history of safe use and is deemed GRAS by the FDA, the small amount of MSG currently used as an additive in foods to enhance taste, and the fact that it is bound up with other proteins when eaten in this manner, eliminates any medical benefit.

The following includes, but is not limited to, some methods to improve bioavailability of the present invention:

In one embodiment, to further enhance bioavailability of the formulation, nanoglobule based nanoemulsion versions may be used to improve solubility. Studies have also shown that encapsulating an anti-inflammatory ingredient into hydrogel nanoparticles (a nano-microparticulate system) yields a homogeneous dispersion in an aqueous solution compared to its free form with a 95% in vitro release profile.

In another embodiment of enhancing the bioavailability while improving the pharmacokinetics of formulae is the use of a copolymer, PLGA (Poly lactic co-glycolic acid), to encapsulate the formulation. This has been shown to provide a more rapid and efficient cellular uptake of the active ingredient.

Intravenous administration of a PLGA enhanced formulation has also been shown to exhibit twice as high serum concentration. PLGA and PLGA-polyethylene glycol (PLGA-PEG) blend nanoparticles containing an active ingredient have been shown to increase the mean bioavailability of the active ingredient after 4-6 hours by a factor of 2.9 and 7.4 fold. These same formulations have also been shown to increase active ingredient bioavailability by 15.6 and 55.4 fold respectively compared to an aqueous suspension. In addition high molecular weight PLGA has been shown to be more effective (40 fold) than low molecular weight PLGA in this application.

In support of these claims, it has been found that relative bioavailability was improved by the addition of PLGA associated with improved water solubility, higher release rate in the intestinal juice, enhanced absorption due to improved permeability, inhibition of P-glycoprotein-mediated efflux, and increased time in the intestinal cavity It has been found that after oral administration of curcumin-PLGA-nanoparticles, the relative bioavailability was increased 5.6-fold and has a longer half-life compared with that of native curcumin. This improved oral bioavailability of curcumin is found to be associated with improved water solubility, higher release rate in the intestinal juice, enhanced absorption by improved permeability, inhibition of P-glycoprotein-mediated efflux, and increased residence time in the intestinal cavity. It has also been observed that PLGA enhanced formulae produce a two to six fold increase in the cellular uptake of cancer cells.

In another embodiment, Liposomes may be used to improve bioavailability due to their ability to solubilize hydrophobic compounds and alter their pharmacokinetic properties. These may be combined with propylene glycol or silica coated for further bio-enhancement and stability.

In another embodiment, use of Cyclic Oligosaccharides (CD), for encapsulation, has also been shown to provide enhanced bioavailability and a greater cellular uptake and longer half-life in cancer cells as well as improved tissue permeability across animal skin.

In another embodiment, Piperine, a major component of black pepper, is widely known as an inhibitor of hepatic and intestinal glucuronidation. The effect of Piperine on the pharmacokinetics of drugs has been shown to be much greater in humans than even lab rats. Studies have shown concomitant administration of Piperine increases bioavailability by enhancing the serum concentration and extent of intestinal absorption up to 20 fold more when used in humans than rats, while remaining significantly longer in the body tissues.

In another embodiment, Hectorite clay, an inert substance, currently used as an extended release agent in therapeutic drugs administered into highly vascular tumors is another method to enhance bioavailability by increasing the residence time in the intestinal cavity and enhancing the extent of intestinal absorption.

Another added benefit of using NaOH is that the slightly alkali formula further neutralizes the acid pH in the diseased and inflammation areas caused by the accretion of lipids and (through binding with dead cells which turns it into a solid or semi solid and, at the same time reducing the production of white blood cells in the area) all part of the problem this formula treats.

The optimal concentration of MSLGM in the oral formula was determined by use on arthritis and gout sufferers.

Increasing the concentration proved to provide no added benefit.

The topical gel versions of this formula (CureZit, Zostrex, Sarcoidex) have been used to successfully treat Acne, Shingles, Herpes 1 & 2. In the case of Shingles, Herpes 1 & 2 and Sarcoidosis it appears to have triggered the body to create its own immunity even where not applied. The diseases stopped spreading and have not reoccurred since (years later).

In one embodiment, the formula for the topical gel version is represented as follows:

Formula 1
Monosodium L-Glutamate Monohydrate 540-840 g;
H2O—2200-3800 g
Propylene Glycol—300-500 g
polyacrylamide based emulsion and rheology modifier—400-600 g
NaOH q.s. to 7.5-9.0 pH Formula 2
Monosodium L-Glutamate Monohydrate 680-720 g;
H2O 2700-3000 g;
Propylene Glycol (humectant for increased absorption) 380-420 g;
polyacrylamide based emulsion and rheology modifier 480-520 g;
NaOH q.s. to 8.5 pH.
Formula 3
Monosodium L-Glutamate Monohydrate 700 g;
H2O 2800 g;
Propylene Glycol (humectant for increased absorption) 400 g;
polyacrylamide based emulsion and rheology modifier 510 g;
NaOH q.s. to 8.5 pH.
One preferred polyacrylamide based emulsion and rheology modifier is commercially available as Sepigel #305 (all of the formula optionally include carbomer for adhesion, thicker coating & preventing recrystallization).

This topical formulation is completely novel and unforeseen as MSLGM requires extended solubility when exposed to air and absorption through skin. The addition of the propylene glycol and the polyacrylamide-based emulsion and rheology modifier is critical to efficacy.

For spray version of gel formula used to treat insect bites and stings only add 26 g Sepigel #305.

Thus, the nasal spray formulated:

Formula 1

Monosodium L-Glutamate Monohydrate 540-840 g;

H2O 2200-3800 g;

Propylene Glycol-300-500 g;

polyacrylamide based emulsion and rheology modifier 20-40 g;

NaOH q.s. to 7.5-9.0 pH.

Formula 2

Monosodium L-Glutamate Monohydrate 680-720 g;

H2O-2700-3000 g;

Propylene Glycol (humectant for increased absorption) 380-420 g;

polyacrylamide based emulsion and rheology modifier 25-35 g;

NaOH q.s. to 8.5 pH.

Formula 3

Monosodium L-Glutamate Monohydrate 700 g;

H2O 2800 g;

Propylene Glycol 400 g;

polyacrylamide based emulsion and rheology modifier 26 g;

NaOH q.s. to 8.5 pH.

In the spray version of the gel formula of the present invention a significant and unforeseen improvement was additionally discovered. MSLGM is a crystal and as such would be unsafe to use with a nebulizer without the spray formula of the present invention in which is imparted beneficiation to make it safe to inhale. Without this formula a patient could not inhale MSLGM and not be able to treat a myriad of respiratory diseases.

The invention provides this list of diseases which have been successfully treated/cured using the MSLGM formulation of the present invention Gout—within 24-48 hours Arthritis (including Rheumatoid and Psoriatic)

Shingles—within 24-48 hours

Acne (including severe, cystic, and adult idiopathic)

Herpes I and Herpes II-Did not reoccur

Sarcoidosis (Equine) within 10 days (did not reoccur)

Cirrhosis (liver regenerated 100%)

Prostate-PSA reduced from 10 to 2

Prostate Cancer—mass shrank and became malleable

Mitral/Aortic Valve Calcification-reversed

Peyronie's Disease-reversed

Cataracts—dissolved

Sebaceous Growths—liquified and were reabsorbed without surgery

COVID-19—Prevention, Cure, triggers self immunity

Insect Bites and Stings Treatment—topical effective on all

Kidney Stones—dissolved stones and prevented recurrence

"Free amino acids" are more commonly known as non-essential (unnecessary) amino acids. This is part of the fallacy of current conventional wisdom and science. The positive results achieved in the present invention surprisingly provides efficacious treatment of diseases using these assumed non-essential "free" amino acids is further proof positive of the novelty of our invention and their "common denominator". The use of the term here is intended to specifically denote that it is "free" to roam, not that it is superfluous and non-essential. Just the opposite—It is absolutely essential for good health and healing.

A completely novel and thus non-obvious use provides:

a) MSG is not known as "an anti-inflammatory ingredient" and its use in combination with nanoparticles is therefore novel.

b) Use of the formula with the nanoparticle system not adversely affecting the efficacy or pH of the formula proves novelty.

In the topical formulation, use of the topical gel version in combination with propylene glycol did not simply improve bioavailability. Without propylene glycol, the MSGLM proved ineffective in topical applications.

The present invention, providing the delivery as described, provides for administration of MSLGM directly, in its optimal absorptive form, to the area where it is needed. Ideally, there must be physical contact. Topical gel to treat shingles, herpes, acne etc. Spray to treat insect bites and stings etc . . . \ Oral to treat arthritis, gout etc. Bloodstream injection to treat leukemia, other forms of cancer.

Regarding the methods of administration, the following are provided:

The liquid composition for oral administration is 100-125 ml by mouth once daily in fasting state as described herein.

Clinical observations will determine subsequent dosing. In one embodiment administration is 1-7 days, although it can be any combination of longer or shorter time as dictated by clinical observation. In one embodiment administration is 1-7 days, although it can be any combination of longer or shorter time as dictated by clinical observation. As generally understood, the method includes identifying a patient with a condition in which oral administration is an effective delivery for providing therapy.

The method for topical administration is also somewhat variable. Terms such as "sparing" application and "liberal" application are often used. The present application contemplates a literature standard of 40-50 g/m2 per application. Although it is recognized vast majority of patients will not measure topical application, the preset invention provides liberal dosing 1-3 times a day.

In one embodiment administration is 1-7 days, although it can be any combination of longer or shorter time as dictated by clinical observation. As generally understood, the method includes identifying a patient with a condition in which topical administration is an effective delivery for providing therapy.

In the method for vapor/nasal administration it is known that the optimal intranasal volume of administration (VOA) for achieving timely and effective is variable. Intranasal medications are typically administered using a mucosal atomization device (MAD), with a commonly recommended optimal VOA of approximately 0.3 mL and a maximum VOA of 1 mL. Other than excess liquid leaking out of the nasal cavity, there are no recognized adverse affects from 1 mL administration. The present invention contemplates nasal dosage of 0.3-1.0 mL per nostril per dose with dosing 3 times daily.

In a method for injectable, the injectable having the same proportions as the oral formulation and 30 cc injected once daily. In one embodiment administration is 1-7 days, although it can be any combination of longer or shorter time as dictated by clinical observation. As generally understood, the method includes identifying a patient with a condition in which nasal administration is an effective delivery for providing therapy.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

What is claimed:

1. An oral liquid composition comprising:
Monosodium L-Glutamate Monohydrate 5-10% w/w;
Water 90-95% w/w;
NaOH q.s. to adjust pH to between 7.5-9.0.

2. The composition of claim 1 wherein said Monosodium L-Glutamate Monohydrate contains not less than 99% relative to H2O on a dried basis based on a non-aqueous titration.

3. The composition of claim 1 wherein said Monosodium L-Glutamate Monohydrate is 7.5-8.6% w/w.

4. The composition of claim 1 wherein said Monosodium L-Glutamate Monohydrate is 8.2-8.5% w/w.

5. The composition of claim 1 wherein said water is 92-93% w/w.

6. A topical composition comprising:
Monosodium L-Glutamate Monohydrate 540-840 g;
H2O 2200-3800 g;
Propylene Glycol 300-500 g;
polyacrylamide based emulsion and rheology modifier 400-600 g;
NaOH q.s. to 7.5-9.0 pH.

7. The topical composition of claim 6 comprising:
Monosodium L-Glutamate Monohydrate 680-720 g;
H2O 2700-3000 g;
Propylene Glycol 380-420 g;
polyacrylamide based emulsion and rheology modifier 480-520 g;
NaOH q.s. to 8.5 pH.

8. The topical composition of claim 6 comprising:
Monosodium L-Glutamate Monohydrate 700 g;
H2O-2800 g;
Propylene Glycol 400 g;
polyacrylamide based emulsion and rheology modifier 510 g;
NaOH q.s. to 8.5 pH.

9. A method of treating; preventing or ameliorating a condition in a human patient, selected from the group consisting of Gout, Arthritis, Shingles, Acne, Herpes I, Herpes II, Sarcoidosis, Cirrhosis, Prostate Cancer, Mitral/Aortic Valve Calcification, Peyronie's Disease, Cataracts, Sebaceous Growths, and Kidney Stones, said method comprising the steps of:

identifying a patient with at least one of Gout, Arthritis, Shingles, Acne, Herpes Herpes H, Sarcoidosis, Cirrhosis, Prostate-PSA, Prostate Cancer, Mitral/Aortic Valve Calcification, Peyronie's Disease, Cataracts, Sebaceous Growths , or Kidney Stones;

administering orally to the patient a composition according to claim 1, wherein said administering must be in a fasting state either two hours after food consumption or two hours prior to food consumption, optionally, administering subsequent doses to the patient as indicated by clinical observation.

10. A method of treating or ameliorating COVID-19 in a human patient, said method comprising the steps of:
identifying a patient with COVID-19;
administering orally to the patient a composition according to claim 1, wherein said administering must be in a fasting state either two hours after food consumption or two hours prior to food consumption,
optionally, administering subsequent doses to the patient as indicated by clinical observation.

11. A method of treating or ameliorating COVID-19 in a human patient, said method comprising the steps of:
identifying a patient with COVID-19;
administering nasally to the patient 0.3 1.0 mL per nostril per dose with dosing 3 times daily, a composition comprising: Monosodium L-Glutamate Monohydrate 5-10% w/w;
Water 90-95% w/w;
NaOH q.s. to adjust pH to between 7.5-9.0;
optionally, administering subsequent doses to the patient as indicated by clinical observation.

* * * * *